United States Patent [19]

LeMoine et al.

[11] Patent Number: 4,923,798

[45] Date of Patent: * May 8, 1990

[54] SALIVA TEST FOR FELINE LEUKEMIA VIRUS

[75] Inventors: Eric D. LeMoine, Poway; Eric S. Bean; Morton A. Vodian, both of Escondido, all of Calif.

[73] Assignee: Synbiotics Corporation, San Diego, Calif.

[ * ] Notice: The portion of the term of this patent subsequent to Aug. 1, 2006 has been disclaimed.

[21] Appl. No.: 169,291

[22] Filed: Mar. 17, 1988

Related U.S. Application Data

[63] Continuation-in-part of Ser. No. 844,098, Mar. 26, 1986, Pat. No. 4,853,325.

[51] Int. Cl.$^5$ ................. G01N 33/569; G01N 33/577
[52] U.S. Cl. ........................................ 435/5; 422/57; 422/58; 422/61; 422/69; 435/7; 435/805; 435/810; 436/518; 436/527; 436/531; 436/548; 436/808; 436/810; 436/811
[58] Field of Search ...................... 435/5, 7, 805, 810; 436/527, 518, 531, 548, 808, 810, 811; 422/57, 58, 61, 69

[56] References Cited

U.S. PATENT DOCUMENTS

| | | | |
|---|---|---|---|
| 4,126,671 | 8/1976 | House et al. | 436/543 |
| 4,379,839 | 2/1980 | Spiegelman | 435/5 |
| 4,582,795 | 6/1983 | Shibuya et al. | 435/34 |
| 4,637,978 | 1/1987 | Dappen | 435/11 |
| 4,663,277 | 5/1987 | Wang | 435/5 |
| 4,689,309 | 8/1987 | Jones | 436/95 |

OTHER PUBLICATIONS

Francis et al, Leukemia Research (1979), 3:435–441 entitled "Feline Leukemia Virus Infections: The Significance of Chronic Viremia".

Francis et al., J. Clin. Pathol. (1979), 32:514–515 entitled "A simple method for quantitating salivary levels of virus using calcium alginate swabs".

Francis et al, J. Clin. Microbiol. (1979), 9:154–156 entitled "Feline Leukemia Virus: Survival Under Home and Laboratory Conditions".

Francis et al., Nature (1977), 269:252–254 entitled "Excretion of feline leukemia virus by naturally infected pet cats".

Hoover et al., Cancer Research (1977), 37:3707–3710 entitled "Relationship between Feline Leukemia Virus Antigen Expression and Viral Infectivity in Blood, Bone Marrow, and Saliva of Cats".

W. P. Collins, John Wiley & Sons (1985), "Alternative Immunoassays", p. 235, Hiramatsu, Clin. Chim. Acta (1981), 117:239–249 entitled "Direct assay of cortisol in human saliva by solid phase radioimmunoassay and its clinical applications".

Lutz et al., J. Clin. Microbiol. (1987), 25:827–831 entitled "Detection of Feline Leukemia Virus Infection in Saliva".

Primary Examiner—Christine M. Nucker
Attorney, Agent, or Firm—Edward S. Irons

[57] ABSTRACT

An immunoassay method and apparatus for diagnosing FeLV-induced, persistent viremia is provided comprising combining a feline saliva sample conveniently obtained with a specially designed probe, with anti-p27 antibodies and detecting complex formation as indicative of the viremia. Preferably, the antibodies are bound to the probe for complex formation.

17 Claims, 1 Drawing Sheet

SALIVA TEST FOR FELINE LEUKEMIA VIRUS

CROSS-REFERENCE TO RELATED APPLICATIONS

This application is a continuation-in-part of application Ser. No. 844,098 filed Mar. 26, 1986, now U.S. Pat. No. 4,853,325, which disclosure is incorporated herein by reference.

INTRODUCTION

1. Technical Field

This application relates to immunoassays for detection of viral antigens, and in particular to an assay for FeLV in saliva.

2. Background of the Invention

Feline leukemia virus is one of the most important infectious causes of death among cats. FeLV-induced diseases include a variety of neoplastic disorders including leukemia and lymphosarcoma, anemia, leukopenia, thrombocytopenia, neurological disorders, reproductive failures in female cats, and a variety of secondary infections caused by FeLV-induced immunosuppression.

FeLV infection usually starts in the lymphoid tissue of the oropharynx and spreads to the bone marrow in two thirds of the infected cats. Once the rapidly-dividing bone marrow cells have become infected, persistent viremia develops, which is followed by the development of FeLV-induced disease in the infected animal together with the ability to infect other cats. Transiently infected animals do not have bone marrow involvement, recover and do not infect other animals. In addition to the oropharynx and bone marrow, FeLV is known to replicate in a number of other tissues including salivary glands, tear ducts, and the epithelial linings of the intestine and the urinary tract. FeLV is transmitted horizontally, most commonly by saliva. Saliva is known to contain between $10^2$ to $10^5$ infectious particles per ml.

Feline leukemia virus has been deteoled by a number of assays which measure a number of different antigens. In particular, a number of ELISA tests of serum detect FeLV group-specific antigens (gsa), the major component of which is the FeLV core protein p27. That assay does not correlate well with persistent viremia as the antigen has been detected in serum of cats with transient infections. The indirect fluorescent antibody technique (IFA) utilizes specific anti-FeLV gsa serum to detect viral antigens in blood leukocytes and platelets. The detection of group-specific antigens in PBLs and platelets was found to correlate well with viremia. However, the test is difficult to perform and analyze, requiring equipment which is generally not available to the clinician. Additionally, tissue culture assays measuring infectious viral particles have been performed on saliva, tear, urine, and tissue samples.

An easy-to-perform assay that correlates with persistent viremia would allow the clinician to determine those cats which can spread the disease without the need to send out a blood sample for IFA analysis.

Relevant Literature

The LEUKASSAY ™ is a micro ELISA test marketed by Pitman-Moore, Inc. (Washington Crossing, N.J.) and described by Mia et al., *Comparative Immunology, Microbiology and Fections Diseases* (1981) 4:111-117. The assay detects FeLV-gsa in serum using polyclonal anti-FeLV antibodies. A similar serum assay is described by Saxinger, *Intervirology* (1981) 15:1-9.

An improved serum assay, described by Lutz et al., *Amer. J. of Vet. Res.* (1983) 44:2054-2059, employs monoclonal antibodies specific for FeLV p27.

A number of studies have investigated the infectivity of FeLV in saliva. See, for example, Francis et al., *J. of Clin. Micro.* (1979) 9:154-156.

A number of techniques and devices for the collection and assay of various antigens in saliva samples have been described. See, for example, Hoover et al., *Cancer Res.* (1977) 37:3707-3719: Francis et al., *J. of Clin. Path.* (1979) 32:4514-4515: Francis et al.. *Leukemia Res.* (1979) 3:435-441: Francis et al., *Nature* (1977) 269:252-254; U.S. Pat. No. 4,444,880, Tom (1984); U.S. Pat. No. 4,305,924, Piasio et al. (1981).

SUMMARY OF THE INVENTION

An immunoassay method for detecting FeLV-induced, persistent viremia is provided. The assay comprises detecting p27 antigen in the saliva of a cat suspected of being infected with FeLV as indicative of persistent viremia where the presence of p27 correlates with bone marrow involvement. This correlation allows one to determine those infectious cats unlikely to recover from the disease and avoids drawing blood.

An improved assay method and collection device for analysis of FeLV in saliva samples are also provided.

DESCRIPTION OF SPECIFIC EMBODIMENTS

Figure 1:
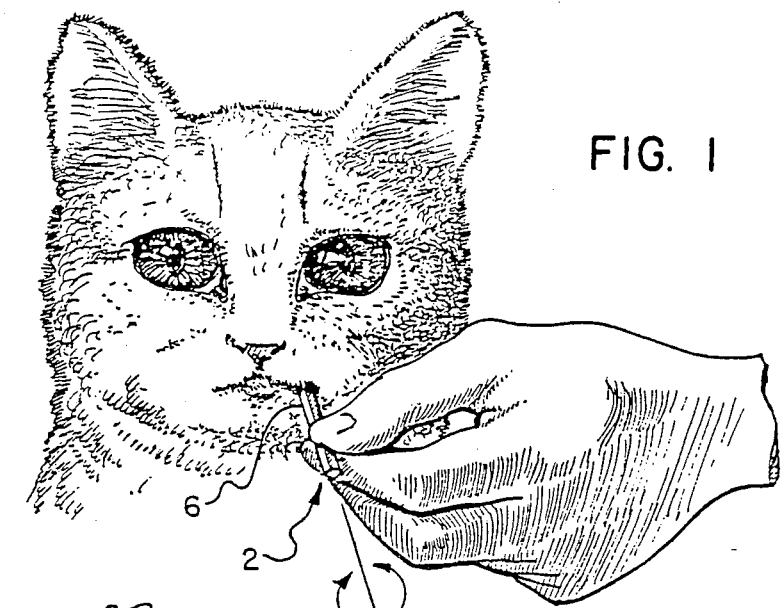
FIG. 1 is a perspective view of an FeLV test probe inserted into a cat's oral cavity towards the buccal crease illustrating the process of rotating the probe.

An immunoassay method for determining whether a cat has FeLV-induced, persistent viremia is provided. The assay comprises detecting p27 antigen in the saliva of a cat suspected of being infected by FeLV. Unlike prior art serum ELISA methods, the present assay correlates with persistent viremia. Further, assays can be performed by a clinician and do not require a blood sample. In a preferred embodiment, a saliva collection device is provided, which device also serves as the solid phase for a sandwich immunoassay.

The assay method has the following elements. The method comprises combining a saliva sample from a cat with anti-p27 antibodies and detecting the presence of antibody-p27 complex as indicative of persistent viremia. The particular manner in which the p27 antigen is detected is not significant for the purpose of this invention so long as the method provides a desired degree of sensitivity and reliability.

A number of different types of immunoassays are well known, using a variety of protocols and labels. The assay conditions and reagents may be any of a variety found in the prior art. The assay may be heterogeneous or homogeneous, usually heterogeneous, conveniently a sandwich assay.

The assay will usually employ solid phase-affixed anti-p27 antibodies. The antibodies may be polyclonal or monoclonal, usually monoclonal. The antibodies are combined with a saliva sample from the cat. Binding between the antibodies and p27 can be determined in a number of ways. For example, any p27 in the saliva sample can compete with a known amount of labeled p27 antigen for antibody binding sites. Alternatively, complex formation can be determined by use of soluble antibodies specific for FeLV p27. The soluble antibodies can be labeled directly or can be detected using labeled second antibodies specific for the species of the soluble antibodies. Various labels include radionuclides, enzymes, fluorescers or the like. Conveniently, the assay will be an enzyme-linked immunosorbent assay (ELISA) in which monoclonal antibodies specific for different epitopes of p27 are used as the solid phase-affixed and enzyme-labeled, soluble antibodies.

A preferred assay method comprises the following steps. A saliva sample from a cat suspected of having FeLV is incubated with solid phase-affixed anti-p27 antibodies for a time sufficient for binding of the antibodies with p27 to form a complex. Conveniently, the amount of complex formation is determined by incubating enzyme-labeled, soluble anti-p27 antibodies with the sample either prior to or after substantial completion of complex formation. The incubation will be for a time sufficient for the soluble antibodies to bind to p27 present in the sample to form a labeled complex bound to the solid phase. Generally the incubation will be for 1 hour or less, usually from about 20 to about 30 min. The soluble antibody is preferably labeled with an enzyme. Alternatively, the soluble antibody may be unlabeled and a second antibody specific for the soluble antibody and from a species source different from the source of the soluble antibody will also be incubated with the sample. The amount of labeled complex is determined by separating the complex from unbound label, conveniently by washing the solid phase.

The solid phase is then incubated with a development solution containing enzyme substrate for a time sufficient for sufficient substrate to react with the enzyme to produce a detectable amount of product, usually for less than 1 hour, conveniently 20 min. or less. A change in the optical density of the development solution is determined as indicative of the persistent viremia. A change in optical density can be determined spectrophotometrically or, conveniently, is capable of being observed visually by a color change of the development solution.

Figures 2, 3, 4, 5, 6:
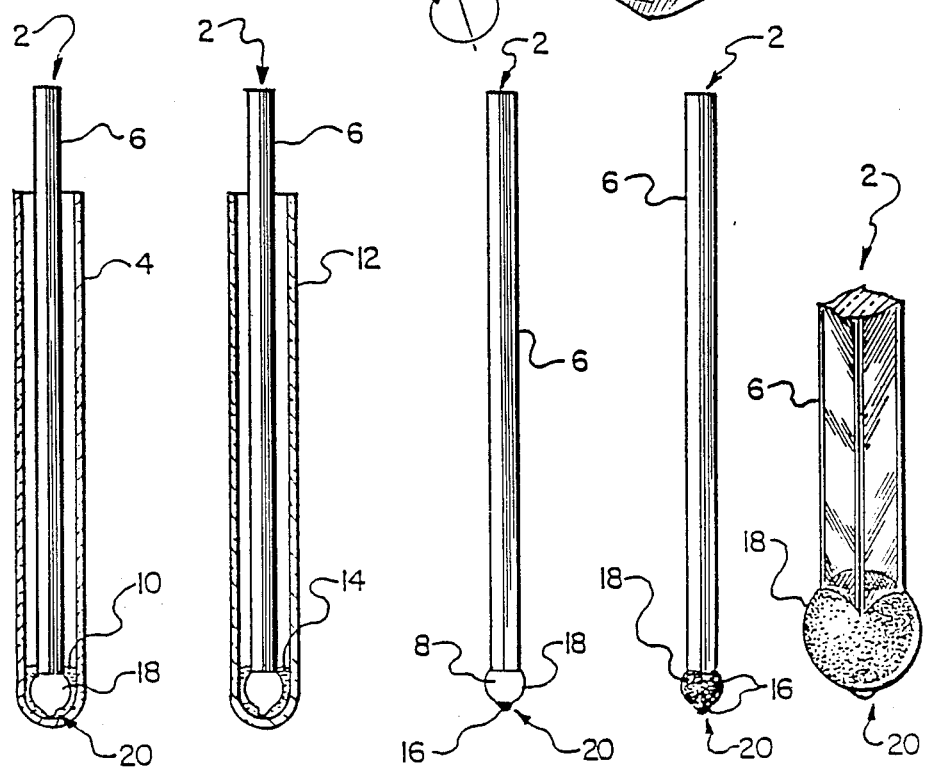
FIG. 2 is a perspective view of the probe of FIG. 1 inserted into an incubation vessel illustrating the submersion of the immunochemically-sensitive member of the probe within an incubation reagent. The nipple-shaped control submember is shown to support the test submember slightly above the bottom of the incubation vessel.
FIG. 3 is a perspective view of the probe of FIG. 2 inserted into a development vessel and submerged in a chromogenic substrate solution.
FIG. 4 is a perspective view of the probe of FIG. 3 illustrating negative color development on the test submember and positive color development on the control submember.
FIG. 5 is a perspective view of the probe of FIG. 3 illustrating positive color development on the test submember and positive color development on the control submember.
FIG. 6 is an enlarged fragmentary view of the probe of FIG. 5 illustrating the frosted texture of the immunochemically-sensitive member with positive color development.

In a preferred embodiment of the assay, an immunological probe is employed to collect and assay a saliva sample. The probe may be a plastic composition, conveniently polystyrene. Referring to FIG. 4, the probe 2 includes an elongated handle 6 and an immunochemically-sensitive member 8. The length of the handle is sufficient to enable a veterinary clinician to insert the probe 2 to the posterior oral cavity between the cat's jaw and the buccal surface. The handle 6 may be approximately 3-4 inches long and 1/28-3/16 inch in diameter.

As shown in FIG. 4, the immunochemically-sensitive member 8 of the probe 2 includes a test submember 18 attached to the handle 6 and, optionally, a control submember 20. The test submember comprises solid phase-affixed anti-p27 antibodies which serve to bind p27 present in the saliva. The control submember provides a portion of the immunochemically-sensitive member that indicates a positive test in the presence of active assay reagents so that one can readily distinguish a negative saliva sample from an assay using inactive reagents.

FIGS. 2-6 illustrate an preferred embodiment having a spherically shaped test submember 18. However, a variety of shapes, e.g. elipsoidal, oblong, oblate, egg shaped, and the like may be employed. As illustrated in FIGS. 4 and 5, the test submember 18 will desirably be shaped for insertion into a cat's buccal crease, the posterior portion of the cat's oral cavity between the jaw and the buccal surface, to conform to the interior configuration of the incubation vessel, to blunt the contact between the immunochemically-sensitive member 8 and the oral cavity, to provide a uniformly wettable surface, and to readily distinguish between the immunochemically-sensitive member 8 and the handle 6.

The test submember 18 may have a spherical shape with the control submember 20 having a nipple-like shape attached to and extending from the test submember 18 axially with the handle 6. The test submember 18 conveniently has a diameter of approximately 3/16-5/16 inch. The surface of the test submember 18 may be etched or frosted. If the probe 2 is composed of polystyrene, this etching or frosting may be provided during the molding process. A frosted surface is advantageous in providing an improved wettability and a comparatively increased surface area.

The test submember 18 may be also adapted to substantially fill an incubation vessel. FIG. 2 illustrates that the diameter of the test submember 18 is only slightly smaller than the inner diameter of the cylindrical incubation vessel 4. The close fit permits a small volume of liquid to completely submerge the test submember 18 in the incubation vessel 4. FIG. 2 also illustrates a nipple-shaped control submember 20 extending from the test submember 18. The control submember 20 extends to the bottom of the incubation vessel 4 and serves to support and raise the test submember 18 off the bottom of the incubation vessel 4. In this manner, liquid within the incubation vessel 4 is uniformly distributed around the test submember 18, minimizing the diffusion distances and thus the duration of the incubation period.

The immunochemically-sensitive member 8 may be coated with one or more types of antibody. The test submember 18 is coated with anti-p27 antibodies, usually monoclonal antibodies, by passive adsorption. The control submember 20 is coated with an antibody specific for the Fc portion of anti-p27 antibody, usually polyclonal anti-mouse IgG antibody. If a control submember is included in the probe, it should be coated prior to coating the test submember 18. The control submember 20 may be coated by incubating the control submember portion for three or four hours at room temperature (25° C.) in a solution of antibody. For example, anti-mouse IgG can be used (2-5 micrograms immunoglobulin/ml) in a suitable buffer, such as pH 9.2 sodium borate buffer. The volume of antibody solution should be sufficiently small so that it covers only the control submember 20 without significant contact with the test submember 18. After the control submember 20 is coated, the test submember 18 may then be coated.

The test submember 18 may be incubated for 3 or 4 hours at room temperature (25° C.) in a solution of anti-p27 antibodies (2-5 micrograms immunoglobulin/ml) in pH 9.2 sodium borate buffer. The anti-p27 antibody may be either polyclonal or monoclonal, usually monoclonal. The volume of anti-p27 immunoglobulin solution should be sufficient to substantially submerge the entire test submember 18. After the test submember 18 is coated with antibody, it may then be coated with BSA to reduce non-specific binding. The coating is conveniently performed by incubating the immunochemically-sensitive test member for three hours in 1% BSA, pH 7.4 PBS. The device is then washed in 0.05% Tween-20, PBS. Optionally, the device may then be coated with a solution that stabilizes the protein such as by preventing crystal formation. A sugar solution, such as 1% (w/w) sucrose, can be used for this purpose. The device is then air dried at room temperature (25° C.) for about 24 hours. For maximum stability, the probes are stored dry at 4° C.

Prior to use, the immunochemically-sensitive member 8 should be washed under water. Washing removes the stabilizer, if present, and pre-wets the device providing for more consistent sample collection, particularly when the cat's mouth is dry. Using the handle 6, the user inserts the washed immunochemically-sensitive member 8 into the cat's buccal crease, as illustrated in FIG. 1. The probe 2 may then be axially rotated within the buccal crease so as to uniformly wet the immunochemically-sensitive member 8 with the cat's saliva. The probe 2 is removed from the cat's oral cavity and transferred to an incubation vessel.

As shown in FIG. 2, the incubation vessel 4 includes an incubating solution 10 having a composition 35 which includes a soluble enzyme conjugate of anti-p27 antibodies in a sufficient volume of assay buffer to submerge the immunochemically-sensitive member 8. Incubation is for a time sufficient for FeLV p27 antigens in the saliva to bind to the immunochemically-sensitive member 8 and for the soluble enzyme conjugate in the incubating solution 10 to bind to both the soluble and immobilized p27 antigens. After incubation, the probe 2 is removed from the incubation vessel and rinsed to remove unbound enzyme conjugate from the immunochemically-sensitive member 8.

After rinsing, the immunochemically-sensitive member 8 of the probe 2 is inserted into a developing vessel 12 containing a developing solution 14 having a chromogenic enzyme substrate in a suitable buffer as illustrated in FIG. 3. The chromogenic enzyme substrate 14 will vary depending on the particular enzyme conjugate used. The choice of enzyme in the conjugate will vary depending on whether precipitable or nonprecipitable color products are desired. Precipitating chromogenic substrates precipitate directly onto the immunochemically-sensitive member 8, as shown in FIGS. 4-6, while nonprecipitating chromogenic substrates 14 cause a color 16 change in the development buffer. As shown in FIG. 4, development of color 16 on the control submember 20 indicates that the enzyme conjugate 10 and the precipitating chromogenic substrate 14 are active. Nonprecipitating chromogenic substrates cannot be used with probes having an integrally attached control submember 20. When using a nonprecipitating chromogenic substrate, a separate device is used with the probe coated with anti-Fc antibody which is incubated in parallel with the sample probe to test the activity of the reagents.

Reagents for performing the assay can be conveniently packaged as a kit. The kit comprises a probe, an incubation vessel, and a development vessel. The kit may also contain a sufficient quantity of incubation solution and development solution to assay the probe(s) included in the kit or those reagents may be provided separately in quantities sufficient for multiple assays. Optionally, the kit will additionally contain instructions for performing the assay and analyzing the results.

In an embodiment useful for clinicians, the kit comprises a plurality of probes, conveniently about 10-20, an incubation vessel and a development vessel for each probe, and bottles of incubation solution and development solution. When the enzyme is horseradish peroxidase, the development solution is usually provided in two bottles A kit for home use conveniently includes a test and a control (positive) probe, two capped incubation vessels, and two capped development vessels, each containing predispensed solutions and, conveniently, instructions for performing and analyzing the assay.

EXPERIMENTAL

To demonstrate the effectiveness of an ELISA assay of saliva in diagnosing FeLV disease, the assay was compared to two currently used FeLV testing methods in a controlled environment and in a clinical situation. Each of the assay methods was used to analyze samples from four experimentally infected specific pathogen-free cats. Four eight-week-old cats were challenged with an intravenous injection of 0.1 ml of a 20% (w/v) FeLV-Rickard tumor homogenate. The cats were assayed daily for FeLV infection by each of the three FeLV testing methods: (i) indirect immunofluorescence assay (IFA) (Hardy et al., In R. M. Dutcher and L. Chieco-Bianchi (ed.), Unifying concepts of leukemia (1973) p. 778-799; Hoover et al., Am. J. Vet. Res. (1978) 39:1877-1880): (ii) FeLV antigen presence in serum by ELISA (Lutz et al., J. Immunol. Methods (1983) 56:209-220), using a ViraChek ELISA kit (Synbiotios) on serum samples which were frozen until use: and (iii) FeLV antigen present in saliva using an ELISA as described below.

The saliva ELISA was performed by a test kit provided by Synbiotics Corporation, San Diego. Calif. The kits consisted of plastic sticks with bulbous ends, as shown in FIGS. 2 and 3, which were coated with monoclonal antibodies to FeLV p27. The bulbous ends were rinsed with sterile water and inserted along the gums of the cats to cover them with saliva. Each probe was then immersed in 0.5 ml of horseradish peroxidase-labeled p27 antibody, which binds to a second epitopic site of p27. After 10 minutes, the probe was removed and rinsed with sterile water. The probe was then immersed in a chromogenic substrate, tetramethylbenzidine (TMB) and urea hydrogen peroxide, and incubated for 10 minutes at room temperature. The appearance of a blue color indicated a positive test.

The results of the assays are shown below in Table 1, as reported in Lewis et al., J. Clin. Microbiol. (1987) 25:1320-1322.

TABLE 1

DIRECT COMPARISON OF THE THREE IMMUNOASSAYS

| Animal No. | Assay | \| | Days | | | | | | | | | | | | | | | | | | | | | | | | |
|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 42 |
| 3477 | Saliva ELISA[a] | − | − | − | − | − | − | − | − | − | − | − | − | + | − | − | − | − | − | − | − | − | − | + | + | + | + | + |
| | IFA[b] | − | − | − | − | − | − | − | − | − | − | − | + | + | + | + | + | + | + | + | + | + | + | + | + | + | + | + |
| | p27 ELISA[c] | − | − | − | − | − | − | + | + | + | + | + | + | + | + | + | + | + | + | + | + | + | + | + | + | + | + | + |
| 3480 | Saliva ELISA | − | − | − | − | − | − | − | − | − | − | − | − | − | − | − | − | + | − | − | + | − | + | + | + | + | + | + |
| | IFA | − | − | − | − | − | − | − | − | − | − | − | + | + | + | + | + | + | + | + | + | + | + | − | + | − | + | + |
| | p27 ELISA | − | − | − | − | − | − | − | − | − | − | − | + | + | + | + | + | + | + | + | + | + | + | + | + | + | + | + |
| 3481 | Saliva ELISA | − | − | − | − | − | − | − | − | − | − | − | − | + | + | + | − | − | + | − | − | − | − | + | + | + | + | + |
| | IFA | − | − | − | − | − | − | − | − | − | − | − | + | + | + | + | + | + | + | + | + | + | + | + | + | + | + | + |
| | p27 ELISA | − | − | − | + | + | + | + | + | + | + | + | + | + | + | + | + | + | + | + | + | + | + | + | + | + | + | + |
| 3482 | Saliva ELISA | − | − | − | − | − | − | − | − | − | − | − | + | − | + | − | − | − | − | + | + | − | + | + | + | + | + | + |
| | IFA | − | − | − | − | − | − | − | − | − | − | − | + | + | + | + | + | + | + | + | + | + | + | + | + | + | + | + |
| | p27 ELISA | − | − | − | − | − | − | − | + | + | + | + | + | + | + | + | + | + | + | + | + | + | + | + | + | + | + | + |

As shown in Table 1, the serum ELISA detects FeLV shortly after infection, before the virus has infected the bone marrow. Detection of FeLV by serum ELLISA was as much as 8 days before a positive IFA. Upon testing positive by either serum ELISA or IFA, the cats remained positive throughout the study. In contrast, the saliva ELISA fluctuated between positive and negative unit day 23 postchallenge. All tests after day 23 were positive until the conclusion of the study at 6 weeks postchallenge. These results demonstrate that the ELISA on saliva samples is positive later in the course of infection, following infection of the bone marrow.

The test results are, thus, consistently positive for infected animals in the clinical situation, since infected cats remain asymptomatic until about day 28 to 30. For use as a screening test to eliminate infected animals from a cattery, the test could be performed and then repeated about three weeks later to ensure that any recently infected animals would be detected.

Comparison of Saliva ELISA and IFA

Twenty-six cats that were serum ELISA-positive were tested with the IFA and saliva ELISA as shown in Table 2.

TABLE 2
COMPARISON OF IFA AND SALIVA ELISA RESULTS IN 26 SERUM ELISA-POSITIVE CATS

| Saliva ELISA Result | No. of IFA Results | |
|---|---|---|
| | + | − |
| + | 15 | 7 |
| − | 0 | 4 |

All 15 IFA-positive cats tested positive by saliva ELISA. Additionally, seven ELISA-positive cats tested negative by IFA. There were four cats which were serum ELISA-positive which were negative in both saliva ELISA and IFA tests. The seven cats which tested negative by IFA but positive by saliva and serum ELISA subsequently died of FeLV or FeLV-related diseases. Some FeLV infections are known to cause dramatic anemia in the host which can in turn cause a false-negative IFA due to the limited number of circulating white cells (Mackay et al., *J. Natl. Cancer Inst.* (1975) 54:1–5).

Although the saliva ELISA does not detect early FeLV infections, the results indicated that it was an effective test for determining virus shedding and viremia and thus for diagnosing clinical and experimental infections of cats with FeLV.

Incubation Solution Formulation

The incubation solution formulation was altered to additionally contain 100 mg/ml of norma mouse IgG to the buffer by adding an appropriate volume of mouse serum to the buffer formulation. The improved formulation resulted in a decreased signal associated with an FeLV-negative saliva sample without affecting the signal associated with positive samples. The formulations used were as follows:

Original Conjugate Solution Formulation
Phosphate Buffered Saline (0.01 M phosphate)
1% BSA
0.1% phenol (.0106 M)
0.0001 M FeSO$_4$
0.5% Tween (available from Sigma Chemical Co)
Horseradish peroxidase labeled monoclonal antibody (antibody purified by saturated ammonium sulfate (SAS) precipitation and ion exchange chromatography)

Conjugate Solution Formulation with Mouse IgG
Phosphate Buffered Saline
6% BSA
0.1% phenol (.0106 M)
0.0001 M FeSO$_4$ (.0028%)
0.5% Tween
Mouse IgG (in the form of SAS cut of mouse serum) 0.1 mg/ml of IgG
Horseradish peroxidase labeled monoclonal antibody Chromogen Solutions
TMB
.25 g TMB per liter (.0009 M) in an 0.1 M acetate citrate buffer pH 5 containing 25% dimethyl formamide Peroxide
0.55 g urea peroxide per liter (.0058 M) in 0.1 M citrate phosphate buffer pH 5 with 0.1% sodium benzoate as preservative (.007 M)

The following table illustrates the results obtained with immunologic probes stored overnight at 4° C. and incubated with incubation solution with and without the mouse serum.

TABLE 3

COMPARISON OF INCUBATION SOLUTION WITH AND WITHOUT MOUSE IgG

| CAT # | −mIgG | +mIgG | −mIgG | +mIgG |
|---|---|---|---|---|
| 1 | + | − | 0.164 | 0.061 |
| 2 | + | − | 0.164 | 0.049 |
| 3 | − | − | 0.062 | 0.028 |
| 4 | − | − | 0.049 | 0.037 |
| 5 | − | − | 0.050 | 0.064 |
| 6 | + | − | 0.250 | 0.057 |
| 7 | trace | − | 0.091 | 0.026 |
| 8 | + | − | 0.150 | 0.050 |
| 9 | − | − | 0.077 | 0.042 |
| 10 | | | | |
| 11 | − | − | 0.017 | 0.086 |
| 12 | − | − | 0.073 | 0.081 |
| 13 | trace | − | 0.134 | 0.023 |
| 14 | + | trace | 0.172 | 0.089 |
| 15 | − | − | 0.070 | 0.034 |
| 16 | − | − | 0.039 | 0.031 |
| 17 | − | − | 0.021 | 0.084 |
| 18 | − | − | 0.060 | 0.046 |
| 19 | − | − | 0.058 | 0.051 |
| 20 | trace | − | 0.075 | 0.013 |
| 21 | trace | wk trace | 0.083 | 0.073 |
| 22 | trace | wk trace | 0.074 | 0.086 |
| 23 | − | − | 0.042 | 0.036 |
| 24 | wk trace | wk trace | 0.072 | 0.067 |
| 25 | +++ | +++ | 1.446 | 1.600 |
| 26 | +++ | +++ | 1.477 | 1.296 |
| 27 | +++ | +++ | 0.948 | 1.378 |
| 28 | +++ | +++ | 1.589 | 1.545 |
| 29 | +++ | +++ | 0.732 | 0.680 |
| 30 | + | + | 0.192 | 0.281 |
| 31 | +++ | +++ | 1.058 | 1.187 |
| 32 | + | + | 0.496 | 0.170 |
| 33 | + | − | 0.163 | 0.059 |
| 34 | − | − | 0.035 | 0.050 |
| 35 | − | − | 0.048 | 0.035 |
| 36 | − | − | 0.019 | 0.024 |
| 37 | trace | − | 0.112 | 0.053 |
| 38 | trace | − | 0.109 | 0.046 |
| 39 | − | − | 0.052 | 0.034 |
| 40 | trace | − | 0.082 | 0.070 |
| 41 | − | − | 0.035 | −0.046 |
| 42 | trace | − | 0.084 | 0.039 |
| 43 | − | − | 0.052 | 0.041 |
| 44 | trace | − | 0.085 | 0.036 |
| 45 | − | − | 0.020 | 0.038 |
| 46 | trace | − | 0.096 | 0.089 |
| 47 | trace | − | 0.109 | 0.050 |
| 48 | − | − | 0.051 | 0.040 |
| 49 | − | − | 0.030 | 0.029 |
| 50 | − | − | 0.061 | 0.042 |
| 51 | − | − | 0.022 | 0.030 |
| 52 | − | − | 0.037 | 0.026 |
| 53 | trace | − | 0.081 | 0.044 |
| 54 | | | | |
| 55 | ++ | ++ | 0.918 | 1.113 |
| 56 | − | − | 0.026 | 0.035 |
| 57 | − | − | 0.032 | 0.032 |
| 58 | − | − | 0.048 | 0.047 |
| 59 | trace | − | 0.088 | 0.061 |
| 60 | − | − | 0.050 | 0.026 |
| 61 | + | − | 0.159 | 0.058 |
| 62 | − | − | 0.071 | 0.051 |
| 63 | − | − | 0.024 | 0.020 |
| 64 | + | − | 0.166 | 0.058 |
| 65 | − | − | 0.027 | 0.028 |
| 66 | − | − | 0.062 | 0.046 |
| 67 | − | − | 0.063 | 0.042 |
| 68 | trace | − | 0.103 | 0.058 |
| 69 | − | − | 0.059 | nd |
| 70 | − | − | 0.059 | 0.035 |
| 71 | − | − | 0.032 | 0.048 |
| 72 | − | − | 0.038 | 0.044 |
| 73 | − | − | 0.039 | 0.037 |
| 74 | − | − | 0.042 | 0.042 |
| 75 | − | − | 0.025 | 0.051 |
| 76 | − | − | 0.062 | 0.029 |
| 77 | trace | − | 0.117 | 0.051 |
| 78 | − | − | 0.034 | 0.038 |
| 80 | − | − | 0.073 | 0.031 |
| 81 | − | − | 0.038 | 0.027 |

The present assay is useful as a rapid screening procedure for removal of infected cats from multiple-cat households. Since the test does not require a blood sample, no stress is placed on the sick animal. The assay thus provides a rapid screening procedure for the presence of FeLV-shedding cats having persistent viremia which is useful for rapid clinical diagnosis, home testing or prescreening before vaccination with an FeLV vaccine.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of determining whether a cat has persistent, FeLV-induced viremia comprising:
    combining a saliva sample from said cat with anti-p27 antibodies; and
    detecting the presence of antibody-p27 complex formation as indicative of persistent, FeLV-induced viremia.

2. A method of claim 1 wherein said antibodies comprise monoclonal antibodies.

3. The method of claim 1, wherein said antibodies comprise polyclonal antibodies.

4. A method of claim 1 wherein said anti-p27 antibodies are affixed to a solid-phase.

5. A method of claim 4 wherein said solid phase of said solid phase-affixed anti-p27 antibodies additionally is a sample-collection probe.

6. A method of determining whether a cat has persistent, FeLV-induced viremia comprising:
    (a) incubating a saliva sample from said cat with solid phase-affixed anti-p27 antibodies and labeled, soluble anti-p27 antibodies for a time sufficient for binding of said antibodies with p27 to form a complex:
    (b) removing unbound antibodies from said solid phase; and
    (c) detecting the presence of label affixed to said solid phase as indicative of persistent, FeLV-induced viremia.

7. The method of claim 6 wherein said label is an enzyme.

8. The method of claim 7 wherein said detection comprises incubating a solution comprising enzyme substrate with said solid phase and detecting a change in optical density of said solution as indicative of the presence of solid phase-affixed label.

9. A method of determining whether a cat has persistent, FeLV-induced viremia comprising:
   (a) incubating a saliva sample from said cat with solid phase-affixed anti-p27 antibodies and enzyme-labeled, soluble anti-p27 antibodies for a time sufficient for binding of said antibodies with p27;
   (b) washing said solid phase;
   (c) incubating said washed solid phase with a development solution comprising enzyme substrate for a time sufficient for enzyme to react with substrate, whereby said enzyme substrate reacts with said enzyme to produce a detectable change in the optical density of said development solution when said enzyme is bound to said solid phase;
   (d) detecting the presence of said change in the optical density in said development solution as indicative of persistent FeLV-induced viremia.

10. The method of claim 9 wherein said change in optical density is capable of being detected visually as a color change of said solution.

11. The method of claim 9 wherein said change in optical density is detected spectrophotometrically.

12. A probe comprising:
   an elongated handle having a length sufficient to enable insertion of said probe into a cat's posterior oral cavity, and
   a spherically-shaped immunochemically-sensitive member connected to said handle comprising immobilized anti-p27 antibodies; and
   a control submember integrally connected to said immunochemically-sensitive member having a nipple shape extending from the immunochemically-sensitive member axially with said handle, said control submember comprising an anti-Fc antibody specific for the species of said anti-p27 antibodies.

13. A probe of claim 12 wherein said immunochemically-sensitive member has a frosted surface.

14. A method of determining whether a cat has persistent, FeLV-induced viremia comprising:
   (a) inserting a probe into said cat's oral cavity, said probe comprising a handle, and an immunochemically-sensitive member connected to said handle, wherein said immunochemically-sensitive member comprises immobilized anti-p27 antibodies;
   (b) contacting the immunochemically-sensitive member of said probe with saliva in the cat'oral cavity;
   (c) incubating said probe with enzyme-labeled, soluble anti-p27 antibodies for a time sufficient for binding of said antibodies with p27;
   (d) washing said probe;
   (e) incubating said washed probe with a development solution comprising enzyme substrate for a time sufficient for enzyme to react with said substrate, whereby said enzyme substrate reacts with said enzyme to produce a detectable change in the optical density of said development solution when said enzyme is bound to said solid phase;
   (f) detecting the presence of said change in the optical density in said development solution as indicative of persistent FeLv-induced viremia.

15. A kit comprising:
   a probe comprising an elongated handle having a length sufficient to enable insertion of said probe into a cat's posterior oral cavity and a spherically-shaped immunochemically sensitive member connected to said handle comprising immobilized anti-p27 antibodies and a control submember integrally connected to said immunochemically sensitive member having a nipple shape extending from the immunochemically sensitive member axially with said handle, said control submember comprising an anti-Fc antibody specific for the species of said anti-p27 antibodies;
   an incubation vessel; and
   a development vessel.

16. The kit of claim 15 additionally comprising an incubation solution in said incubation vessel or in a separate container and a development solution in said development vessel or in a separate container.

17. The kit of claim 15 additionally comprising instructions for performing and analyzing the results of said assay, wherein said instructions indicate that positive results of said assay are indicative of persistent, FeLV-induced viremia rather than transient FeLV infection. viremia rather than transient FeLV infection.

* * * * *